United States Patent
Coyle et al.

(10) Patent No.: US 7,208,001 B2
(45) Date of Patent: Apr. 24, 2007

(54) CATHETER WITH DETACHED PROXIMAL INFLATION AND GUIDEWIRE SHAFTS

(75) Inventors: Noel Coyle, Galway (IE); Patrick Duane, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 630 days.

(21) Appl. No.: 10/421,906

(22) Filed: Apr. 24, 2003

(65) Prior Publication Data

US 2004/0215165 A1 Oct. 28, 2004

(51) Int. Cl.
*A61M 29/00* (2006.01)

(52) U.S. Cl. .................. 606/194; 604/96.01

(58) Field of Classification Search ........... 606/192, 606/194, 1; 604/96.01, 102.02, 102.03, 103.04
See application file for complete search history.

(56) References Cited

U.S. PATENT DOCUMENTS

| | | | |
|---|---|---|---|
| 4,748,982 A | 6/1988 | Horzewski et al. | |
| 4,762,129 A | 8/1988 | Bonzel | |
| 4,988,356 A | 1/1991 | Crittenden et al. | |
| 5,040,548 A | 8/1991 | Yock | |
| 5,061,273 A | 10/1991 | Yock | |
| 5,149,330 A | 9/1992 | Brightbill | |
| 5,171,222 A | 12/1992 | Euteneuer et al. | |
| 5,178,158 A | 1/1993 | de Toledo | |
| 5,205,822 A | 4/1993 | Johnson et al. | |
| 5,217,435 A | 6/1993 | Kring | |
| 5,232,445 A | 8/1993 | Bonzel | |
| 5,263,932 A | 11/1993 | Jang | |
| 5,290,241 A | 3/1994 | Kraus et al. | |
| 5,300,085 A | 4/1994 | Yock | |
| 5,324,269 A | 6/1994 | Miraki | |
| 5,327,885 A | 7/1994 | Griffith | |
| 5,334,187 A | 8/1994 | Fischell et al. | |
| 5,336,184 A | 8/1994 | Teirstein | |
| 5,350,395 A | 9/1994 | Yock | |
| 5,357,978 A | 10/1994 | Turk | |
| 5,364,376 A | 11/1994 | Horzewski et al. | |
| 5,370,616 A * | 12/1994 | Keith et al. ............ | 604/102.02 |
| 5,387,226 A | 2/1995 | Miraki | |
| 5,389,087 A | 2/1995 | Miraki | |
| 5,409,459 A | 4/1995 | Gambale | |
| 5,451,233 A | 9/1995 | Yock | |
| 5,458,639 A | 10/1995 | Tsukashima et al. | |
| 5,460,185 A | 10/1995 | Johnson et al. | |
| 5,466,222 A | 11/1995 | Ressemann et al. | |
| 5,489,271 A | 2/1996 | Andersen | |
| 5,496,346 A | 3/1996 | Horzewski et al. | |
| 5,501,227 A | 3/1996 | Yock | |
| 5,531,700 A | 7/1996 | Moore et al. | |

(Continued)

*Primary Examiner*—Sharon E. Kennedy

(57) ABSTRACT

A balloon catheter includes a full-length inflation shaft and a guidewire shaft for fast catheter and guidewire exchange. The proximal portions of the inflation shaft and the guidewire shaft are detached from one another. The detached proximal shaft portions transition within a conversion portion of the catheter shaft and become coaxial within a distal portion of the catheter shaft. The proximal portion of the guidewire shaft may contain a continuous, longitudinally extending slot that acts as a guide member or guidewire track. Alternatively, the proximal portion of the guidewire shaft maybe removable from the catheter at a conversion joint via a snap-fit connection. Both embodiments allow for catheter exchange without removing the guidewire from a body lumen, or allow guidewire exchange without removing the catheter from the body lumen.

11 Claims, 5 Drawing Sheets

U.S. PATENT DOCUMENTS

| | | |
|---|---|---|
| 5,549,556 A | 8/1996 | Ndondo-Lay et al. |
| 5,571,094 A | 11/1996 | Sirhan |
| 5,578,009 A | 11/1996 | Kraus et al. |
| 5,626,600 A | 5/1997 | Horzewski et al. |
| 5,685,312 A | 11/1997 | Yock |
| 5,709,658 A | 1/1998 | Sirhan et al. |
| 5,718,680 A | 2/1998 | Kraus et al. |
| 5,749,888 A | 5/1998 | Yock |
| 5,755,685 A | 5/1998 | Andersen |
| 5,769,868 A | 6/1998 | Yock |
| 5,779,671 A | 7/1998 | Ressemann et al. |
| 5,807,355 A | 9/1998 | Ramzipoor et al. |
| 5,919,164 A | 7/1999 | Andersen |
| 5,919,175 A | 7/1999 | Sirhan |
| 5,947,925 A | 9/1999 | Ashiya et al. |
| 5,947,927 A | 9/1999 | Mertens |
| 5,976,107 A | 11/1999 | Mertens et al. ........ 604/164.13 |
| 5,984,945 A * | 11/1999 | Sirhan ........................ 606/194 |
| 6,013,068 A | 1/2000 | Spiegelhalter |
| 6,036,715 A | 3/2000 | Yock |
| 6,056,719 A | 5/2000 | Mickley |
| 6,096,009 A | 8/2000 | Windheuser et al. |
| RE36,857 E | 9/2000 | Euteneuer et al. |
| 6,165,197 A | 12/2000 | Yock |
| 6,196,995 B1 | 3/2001 | Fagan |
| 6,299,595 B1 | 10/2001 | Dutta et al. |
| 2001/0037085 A1 | 11/2001 | Keith et al. ............... 604/96.01 |
| 2003/0191491 A1 | 10/2003 | Duane et al. |

\* cited by examiner

CATHETER WITH DETACHED PROXIMAL INFLATION AND GUIDEWIRE SHAFTS

BACKGROUND OF THE INVENTION

1. Field of the Invention

The present invention relates to a medical device. More specifically, the invention relates to a catheter that allows fast exchange thereof, and a full-length guidewire lumen that allows fast exchange of a guidewire.

2. Background of the Invention

Cardiovascular disease, including atherosclerosis, is the leading cause of death in the U.S. One method for treating atherosclerosis and other forms of coronary narrowing is percutaneous transluminal coronary angioplasty, commonly referred to as "angioplasty" or "PTCA". The objective in angioplasty is to enlarge the lumen of the affected coronary artery by radial hydraulic expansion. The procedure is accomplished by inflating a balloon of a balloon catheter within the narrowed lumen of the coronary artery. Radial expansion of the coronary artery occurs in several different dimensions, and is related to the nature of the plaque. Soft, fatty plaque deposits are flattened by the balloon, while hardened deposits are cracked and split to enlarge the lumen.

One or multiple dilations maybe necessary to effectively dilate the artery. In many instances, successive dilations using a succession of balloon catheters with balloons of increasingly larger diameters may be required. In order to accomplish the multiple dilations, the original catheter must be removed and a second balloon catheter tracked to the lesion. When catheter exchange is desired, it is advantageous to leave the guidewire in place while the first catheter is removed in order to insert the second catheter without having to reestablish the path by inserting a new guidewire. To remove a balloon catheter while leaving the guidewire in place, there must be a portion of the guidewire extending out of the balloon catheter at the proximal end so that the guidewire can be held in place while the balloon catheter is removed.

Two types of catheters commonly used in angioplasty procedures are referred to as over-the-wire (OTW) catheters and rapid exchange (RX) catheters. A third type of catheter with preferred features of both OTW and RX catheters, that is sold under the trademarks MULTI-EXCHANGE, ZIPPER MX, ZIPPER, and/or MX is discussed below. An OTW catheter's guidewire shaft runs the entire length of the catheter and is attached to, or enveloped within, an inflation shaft. Thus, the entire length of an OTW catheter is tracked over a guidewire during a PTCA procedure. A RX catheter, on the other hand, has a guidewire shaft that extends within only the distalmost portion of the catheter. Thus, during a PTCA procedure only the distalmost portion of a rapid exchange catheter is tracked over a guidewire.

If a catheter exchange is required while using a standard OTW catheter, the user must add an extension onto the proximal end of the guidewire to maintain control of the guidewire, slide the catheter off of the extended guidewire, slide the new catheter onto the guidewire and track back into position. Multiple operators are required to hold the extended guidewire in place while the original catheter is changed out.

A RX catheter avoids the need for multiple operators when changing out the catheter and therefore is often referred to as a "single operator" catheter. With a rapid exchange catheter, the guidewire is outside the shaft of the catheter for all but the distalmost portion of the catheter. The guidewire can be held in place without an extension when the catheter is removed from the body. Once the original catheter is removed, a subsequent catheter may be threaded onto the in place guidewire and tracked to the lesion. However, one problem associated with RX catheters is that the exposed portion of the guidewire may become tangled with the catheter shaft during use.

In addition, there are instances when the guidewire and not the catheter must be replaced. For example, the guidewire may become damaged during the procedure or it may be discovered during the procedure that a different shape, length, or size of guidewire is needed. An OTW catheter, with the guidewire lumen extending the entire length of the catheter, allows for simple guidewire exchange. With a RX catheter, the guidewire lumen does not extend the entire length of the catheter. Therefore, the guidewire, and most of the catheter, must be removed from the body in order to exchange guidewires. Essentially the procedure must then start anew because both the guidewire and the catheter must be retracked to the treatment site.

A balloon catheter capable of both fast and simple guidewire and catheter exchange is particularly advantageous. A catheter designed to address this need sold by Medtronic AVE, Inc. of Santa Rosa, California under the trademarks MULTI-EXCHANGE, ZIPPER MX, ZIPPER and/or MX (hereinafter referred to as the "MX catheter") is disclosed in U.S. Pat. No. 4,988,356 to Crittenden et al., incorporated in its entirety herein by reference. The MX catheter includes a catheter shaft having a cut that extends longitudinally along the catheter shaft and that extends radially from a guidewire lumen to an outer surface of a catheter shaft. A guide member through which the shaft is slidably coupled cooperates with the cut such that a guidewire may extend transversely into or out of the guidewire lumen at any location along the cut's length. By moving the shaft with respect to the guide member, the effective over-the-wire length of the MX catheter is adjustable.

When using the MX catheter, the guidewire is maneuvered through the patient's vascular system such that a distal end of the guidewire is positioned across the treatment site. With the guide member positioned near a distal end of the catheter, a proximal end of the guidewire is threaded into a guidewire lumen opening at the distal end of the catheter and out through the guide member such that the proximal end of the guidewire protrudes out a proximal end of the guide member. By securing the guide member and the proximal end of the guidewire in a fixed position, the catheter may then be transported over the guidewire by advancing the catheter toward the guide member. In doing so, as the catheter advances toward the guide member, the guidewire lumen envelops the guidewire and the catheter is advanced into the patient's vasculature. In a PTCA embodiment, the MX catheter maybe advanced over the guidewire in this manner until the distal end of the catheter having the dilatation balloon is positioned within the stenosis and essentially the entire length of the guidewire is encompassed within the guidewire lumen.

Furthermore, the indwelling MX catheter may be exchanged with another catheter by reversing the operation described above. To this end, the indwelling catheter may be removed by withdrawing the proximal end of the catheter from the patient while holding the proximal end of the guidewire and the guide member in a fixed position. When the catheter has been withdrawn to the point where the distal end of the slot has reached the guide member, the distal portion of the catheter over the guidewire is of a sufficiently short length that the catheter may be drawn over the proximal end of the guidewire without releasing control of the guidewire or disturbing its position within the patient. After the catheter has been removed, another catheter may be threaded onto the guidewire and advanced over the guidewire in the same manner described above with regard to the MX catheter. The MX catheter not only permits catheter exchange without the use of the very long exchange guidewire and without requiring withdrawal of the initially placed guidewire, but it also overcomes many of the other difficulties discussed in association with RX catheters.

It is among the general objects of the invention to provide an alternate catheter which allows for simple guidewire exchange and fluid delivery. Specifically, what is needed is a catheter, which allows for fast catheter and/or guidewire exchange, and which avoids the limitations associated with prior art catheter designs. Accordingly, there arises a need for a catheter having a guidewire shaft and an inflation shaft, wherein a proximal portion of the guidewire shaft is detached from a proximal portion of an inflation shaft at a conversion joint positioned distal of a proximal end of the catheter, that allows for fast catheter and guidewire exchange.

BRIEF SUMMARY OF THE INVENTION

To achieve the foregoing and other objects, and in accordance with the purposes of the present invention as embodied and broadly described herein, the catheter of the present invention provides a catheter that allows rapid catheter exchange without the use of an exchange guidewire, while also allowing for simple and fast guidewire exchange.

A catheter according to the present invention may form the basis of a stent delivery system, an angioplasty catheter, or a drug delivery catheter. A catheter according to the present invention includes a full-length guidewire shaft and inflation shaft that each extend from a proximal end of the catheter to a distal end thereof. The guidewire shaft acts as a full-length conduit for a guidewire, but is constructed to allow for ready access of a proximal end of the guidewire via a proximal guidewire "exit." A position of the proximal guidewire exit along a proximal portion of the guidewire shaft is changeable, and can be located distally of a proximal end of the catheter.

The inflation shaft includes an inflation lumen therethrough that provides fluid communication between an inflation hub at a proximal end thereof and a dilatation balloon at a distal end thereof. The dilatation balloon is mounted at a distal end of the coaxial portion of the catheter shaft according to the present invention to be in fluid communication with the distal end of the inflation lumen. The dilation balloon can be of any shape or size customarily used in angioplasty or stent delivery procedures. The inflation hub is provided to fluidly connect an inflation fluid source at the proximal end of the inflation shaft to an interior of the dilation balloon at a distal end of the inflation shaft.

In a catheter according to the present invention, the proximal portion of the guidewire shaft is detached from a proximal portion of the inflation shaft, and a distal portion of the guidewire shaft is coaxial with a distal portion of the inflation shaft. The coaxial portion of the catheter shaft extends from a proximal end of the balloon to a catheter shaft conversion portion, which is preferably located, but not limited to, a distance of between 15 and 30 centimetres proximal of the proximal end of the balloon. Within the conversion portion of the catheter the detached proximal portions of the inflation and guidewire shafts transition to the coaxial distal shaft arrangement.

In one embodiment of a catheter according to the present invention, the guidewire shaft is comprised of a single full-length tube having a guidewire lumen that extends the entire length of the catheter. A proximal portion of the guidewire shaft extends from a proximal end of the catheter to the catheter shaft conversion portion preferably located, but not limited to, between 15 and 30 centimetres proximal of a balloon. The guidewire shaft proximal portion is detached from a proximal portion of an inflation shaft and includes a continuous longitudinal opening along its length, i.e., a guide member track, and a MX guide member slidably receivable therein. The MX guide member includes a proximal guidewire exit that allows a guidewire ingress and egress to the guidewire lumen.

In the single-shaft MX embodiment of the present invention, the position of the proximal guidewire exit maybe changed according to a user's requirements by sliding the MX guide member along the guide member track. In this manner, the catheter includes a full-length guidewire lumen for fast guidewire exchange when the proximal guidewire exit is at its proximalmost position and allows for fast catheter exchange when the proximal guidewire exit is positioned distally along the guidewire shaft.

In another embodiment of a catheter according to the present invention, the guidewire shaft is comprised of two interconnecting shaft portions that connect in a snap-fit arrangement. In the snap-fit embodiment, the detached proximal portion of the guidewire shaft is removable from a distal portion of the guidewire shaft at a conversion joint within the catheter shaft conversion portion. The conversion portion of the catheter is where the detached proximal portions of the guidewire and inflation shafts transition into a coaxial shaft arrangement in a distal portion of the catheter as discussed above.

In this embodiment of the invention, the catheter shaft conversion joint includes a female fitting that is disposed or integrally formed on a proximal end thereof. The female fitting is formed to interlock with a male fitting disposed on a distalmost portion of the removable, proximal portion of the guidewire shaft. Thus, when the proximal portion of the guidewire shaft is attached to the distal coaxial portion of the catheter, via the snap-fit arrangement of the male and female fittings, the catheter includes a full-length guidewire lumen. However, when the proximal portion of the guidewire shaft is detached from the distal coaxial portion of the catheter, the female fitting of the conversion joint acts as a proximal guidewire exit and allows for fast catheter exchange.

BRIEF DESCRIPTION OF THE DRAWINGS/FIGURES

The foregoing and other features and advantages of the invention will be apparent from the following, more particular description of a preferred embodiment of the invention, as illustrated in the accompanying drawings.

FIG. 1A is a cross-sectional view along line A—A of FIG. 1.

FIG. 3A is a cross-sectional view along line A—A of FIG. 3.

DETAILED DESCRIPTION OF THE INVENTION

Preferred embodiments of the present invention are now described with reference to the figures, where like reference numbers indicate identical or functionally similar elements. Also in the figures, the left most digit of each reference number corresponds to the figure in which the reference number is first used. While specific configurations and arrangements are discussed, it should be understood that this is done for illustrative purposes only. A person skilled in the relevant art will recognize that other configurations and arrangements can be used without departing from the spirit and scope of the invention.

Figure 1:
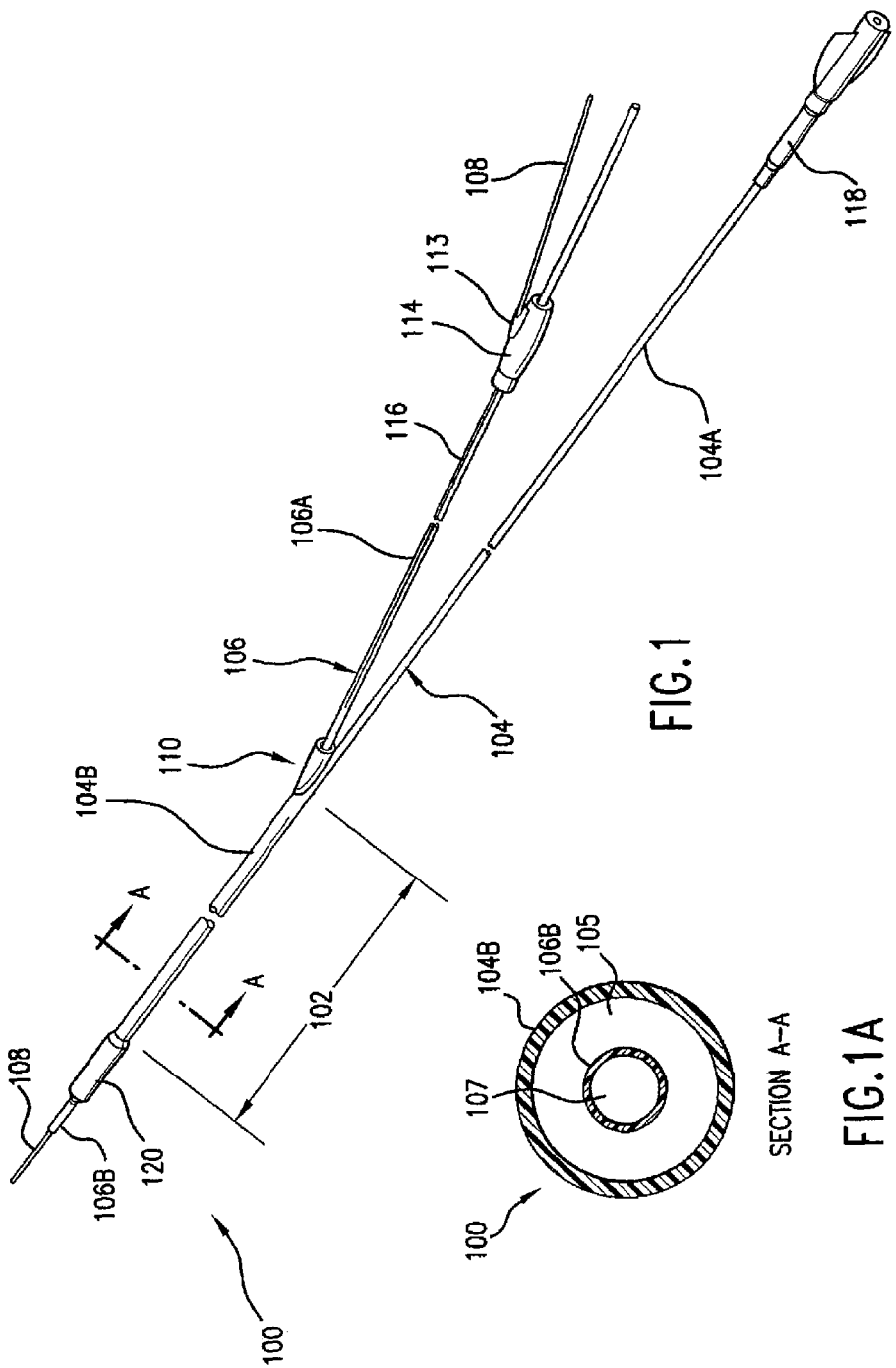
FIG. 1 is a perspective view of an embodiment of a catheter according to the present invention.

Referring to FIG. 1, an embodiment of a balloon catheter 100 according to the present invention is shown. Balloon catheter 100 is shown having an inflation hub 118 at a proximal end thereof and a balloon 120 at a distal end thereof. Catheter 100 includes an inflation shaft 104 having a detached proximal portion 104A fluidly coupled to hub 118 and a distal portion 104B fluidly coupled to balloon 120, such that an inflation fluid can be fluidly communicated there through from a source (not shown) to balloon 120.

Catheter 100 also includes a full-length guidewire shaft 106 having a detached proximal portion 106A and a distal portion 106B. A guidewire 108 is shown entering a proximal guidewire exit 113 of a guide member 114 that is slidably mounted on proximal guidewire shaft portion 106A and exiting distal guidewire shaft portion 106B. Proximal portion 106A contains a continuous, longitudinally extending slot that forms a guide member track 116. In an embodiment of the present invention, guide member track 116 allows access to guidewire 108 along the entire length of guidewire shaft proximal portion 106A through guide member 114. Guide member 114 is further described below. As shown in FIG. 1A, a coaxial distal shaft portion 102 of balloon catheter 100 is comprised of inflation shaft distal portion 104B coaxially disposed about guidewire shaft distal portion 106B.

A conversion portion 110 is located along catheter 100 where the detached, proximal portions of the guidewire and inflation shafts transition to coaxial distal shaft portion 102. Thus, as proximal portion 106A of guidewire shaft 106 proceeds distally through conversion portion 110, it becomes enveloped by and/or concentric with distal portion 104B of inflation shaft 104 in distal shaft portion 102. In forming conversion portion 110, a sufficiently sized mandrel or wire traverses proximal portion 106A and distal portion 106B of guidewire shaft 106. To link the two shaft portions a heat treatment is applied such that the polymer of the shafts flows around the mandrel and melts together to form a strong joint and a continuous guidewire lumen therebetween. For the snap-fit variation, a micro-molded component is formed which accepts the corresponding distal and proximal shafts. These shafts are then heat or ultrasonically welded to the molded component or adhesively bonded, thereby forming the conversion portion.

As shown in FIG. 1A, an inflation lumen 105 is formed between an inner surface of inflation shaft distal portion 104B and an outer surface of guidewire shaft distal portion 106B. Further, guidewire shaft 106 includes a guidewire lumen 107 that extends up to the full length of catheter 100.

Inflation shaft proximal portion 104A is made up of a relatively stiff material (e.g. stainless steel hypotube). Distal of conversion joint 10, inflation shaft distal portion 104B is made up of any of the following materials: polyethylene terephalate (PET), which allows for very thin walls while withstanding high inflation pressures; nylon, which provides a soft material; and polyethylene, which is advantageous for its compatibility with new angioplasty techniques, such as lasers. Guidewire shaft 106 is made of HDPE. Non-exhaustive examples of material for guidewire shaft 106 include polyethylene, PEBAX, nylon or combinations of any of these.

At conversion portion 110 of the catheter, a conversion bond is formed between guidewire shaft 106 and inflation shaft portion 104A and 104B to secure the shafts to one another, and to ensure a smooth transition between the detached proximal portions of the guidewire and inflation shafts and the coaxial distal shaft portion 102. In forming the conversion bond, a support mandrel, or wire, is placed within guidewire shaft 106 to traverse the bonding area to ensure that the guidewire lumen remains open after the bond formation, as discussed above.

Figure 2:
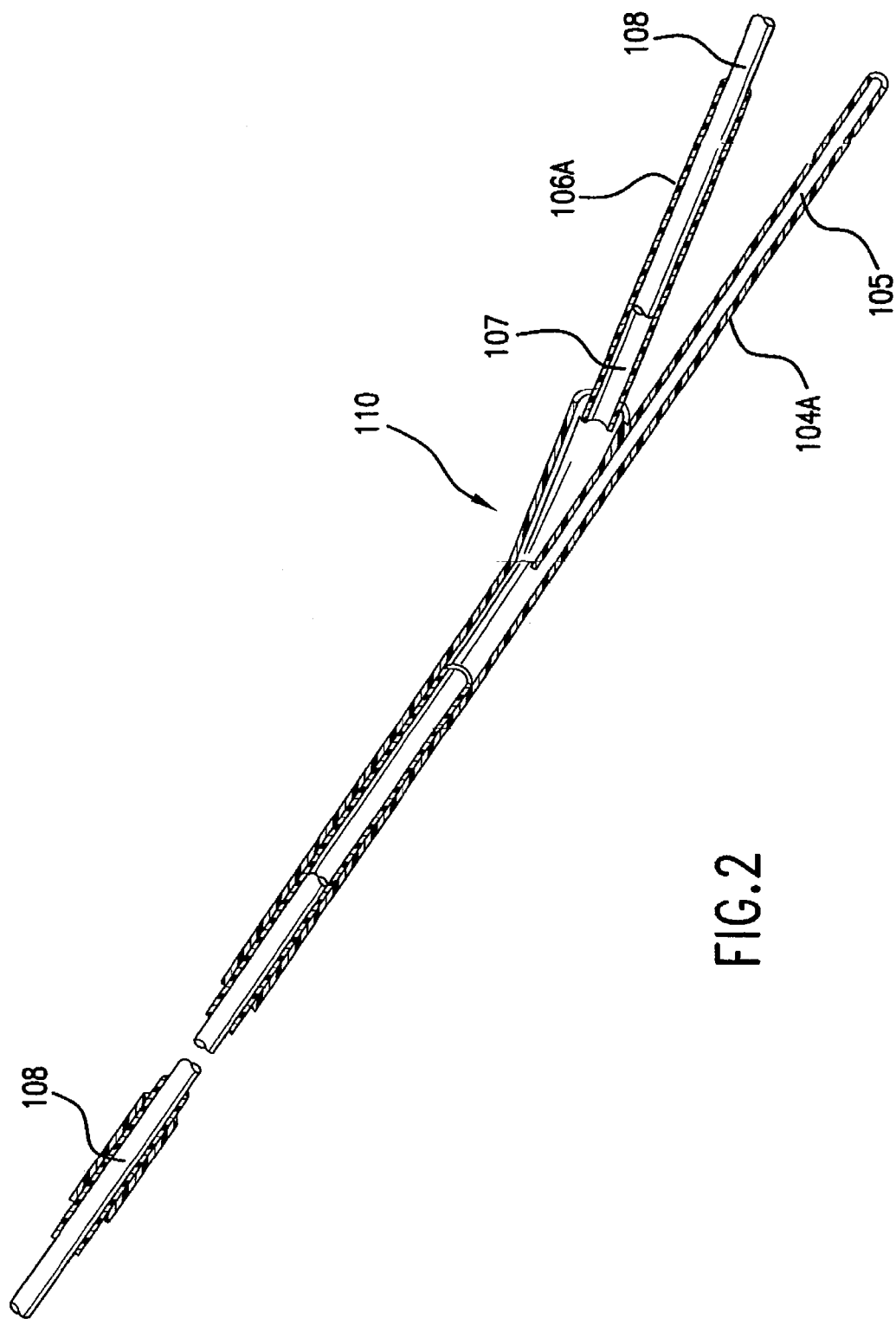
FIG. 2 is a sectional view of a portion of the catheter shown in FIG. 1.

FIG. 2 is a sectional view of a portion of catheter 100 shown in FIG. 1. As shown in FIG. 2, proximal portion 104A of inflation shaft 104 and proximal portion 106A of guidewire shaft 106 are independent and separate from one another.

At conversion portion 110 of the catheter, a conversion bond is formed between guidewire shaft 106 and inflation shaft portions 104A and 104B to secure the shafts to one another, and to ensure a smooth transition between the detached proximal portions of the guidewire and inflation shafts and coaxial distal shaft portion 102. In forming the conversion bond, a support mandrel, or wire, is placed within guidewire shaft 106 to traverse the bonding area to ensure that the guidewire lumen remains open after bond formation.

A support mandrel is also placed within the guidewire lumen during formation of guide member track 116. With the support mandrel in place within the proximal portion of the guidewire shaft, the longitudinally extending slot that acts as guide member track 116 may be formed using either a single, moveable blade, a 'collet'-type arrangement of numerous blades, or by directional laser. After guide member track 116 is formed, the support mandrel is removed.

Guide member track 116 allows for faster catheter exchanges without the use of an exchange guidewire. With the present invention, the user may slide an indwelling catheter 100 proximally while maintaining contact with indwelling guidewire 108. As catheter 100 is removed from the patient's vasculature, guide member 114 is slid distally along guide member track 116 such that the operator maintains contact with and control of guidewire 108. At or before guide member 114 reaches conversion portion 110, control of guidewire 108 shifts from just proximal of conversion portion 110 to a point at a distalmost tip of catheter 100. Once catheter 100 is removed from the guidewire, a second catheter may be backloaded onto indwelling guidewire 108 and tracked to the site of treatment. The detached proximal portion 106A of guidewire shaft 106 gives the user fuller control over the exposed guidewire by allowing the user to manipulate the wire as required or allowing the user to maintain the wire's position during manipulation of catheter 100.

Elongated guidewire shaft 106 allows for simple and fast guidewire exchange. To change a guidewire, the user can pull the indwelling guidewire out of guidewire shaft 106 through guide member 114 at any point along guide member track 116 of guidewire shaft proximal portion 106A, and feed a new guidewire into proximal guidewire exit 113 while catheter 100 remains in position within a body lumen. In this manner, elongated guidewire shaft 106 envelops guidewire 108 along its entire length and prevents the problem of a proximal portion of an inflation shaft becoming entangled with the external portion of the guidewire, which may occur during use of a rapid exchange catheter.

Figure 3:
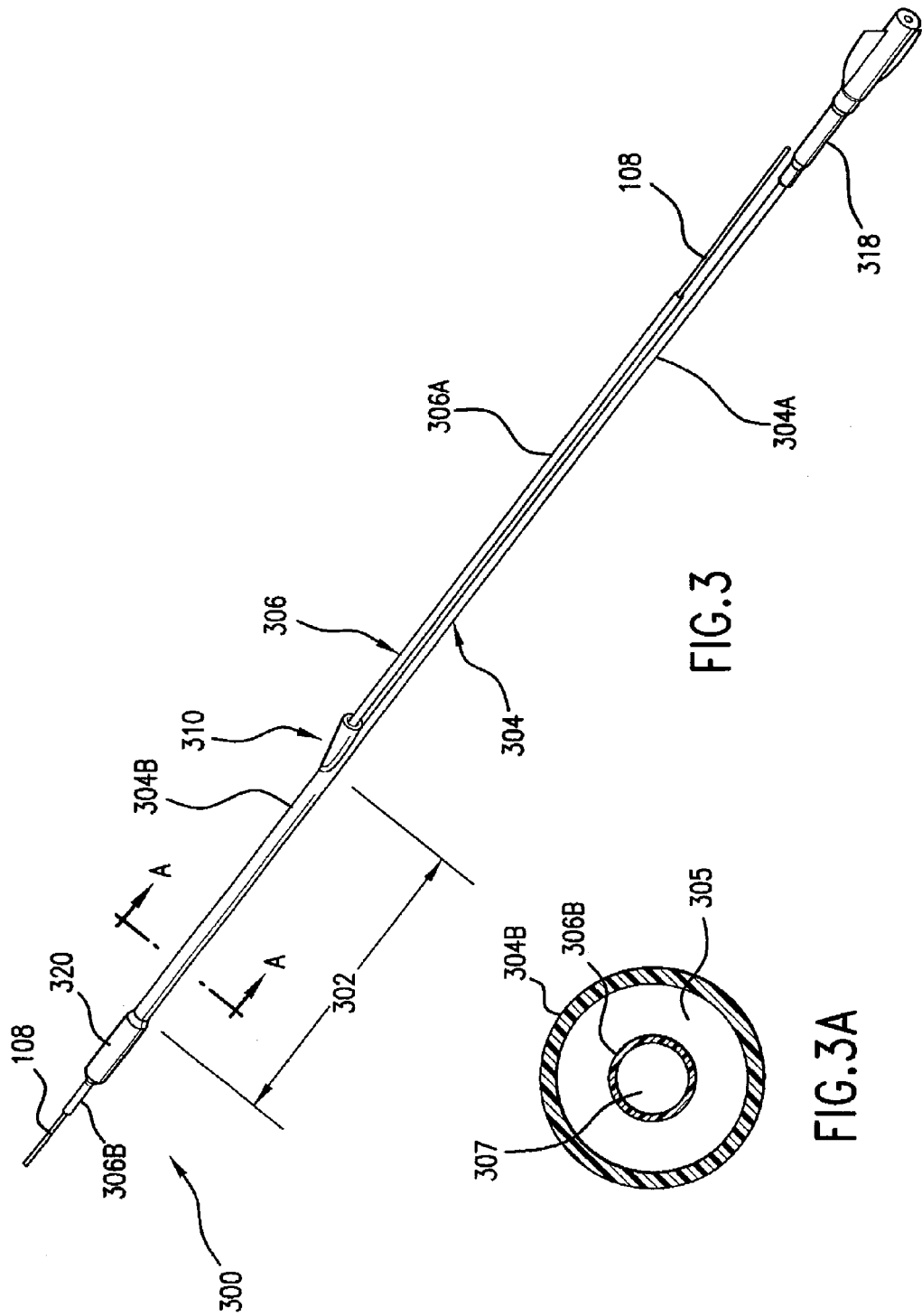
FIG. 3 is a perspective view of another embodiment of a catheter according to the present invention.

FIG. 3 is an alternate embodiment of a catheter 300 according to the present invention. Particularly, a conversion joint 310 and a proximal portion 306A of guidewire shaft 306 are joined by a snap-release/snap-lock arrangement. Proximal guidewire shaft detached portion 306A is removable at conversion joint 310, thereby permitting access to and control of a proximal end of guidewire 108.

Figure 4:
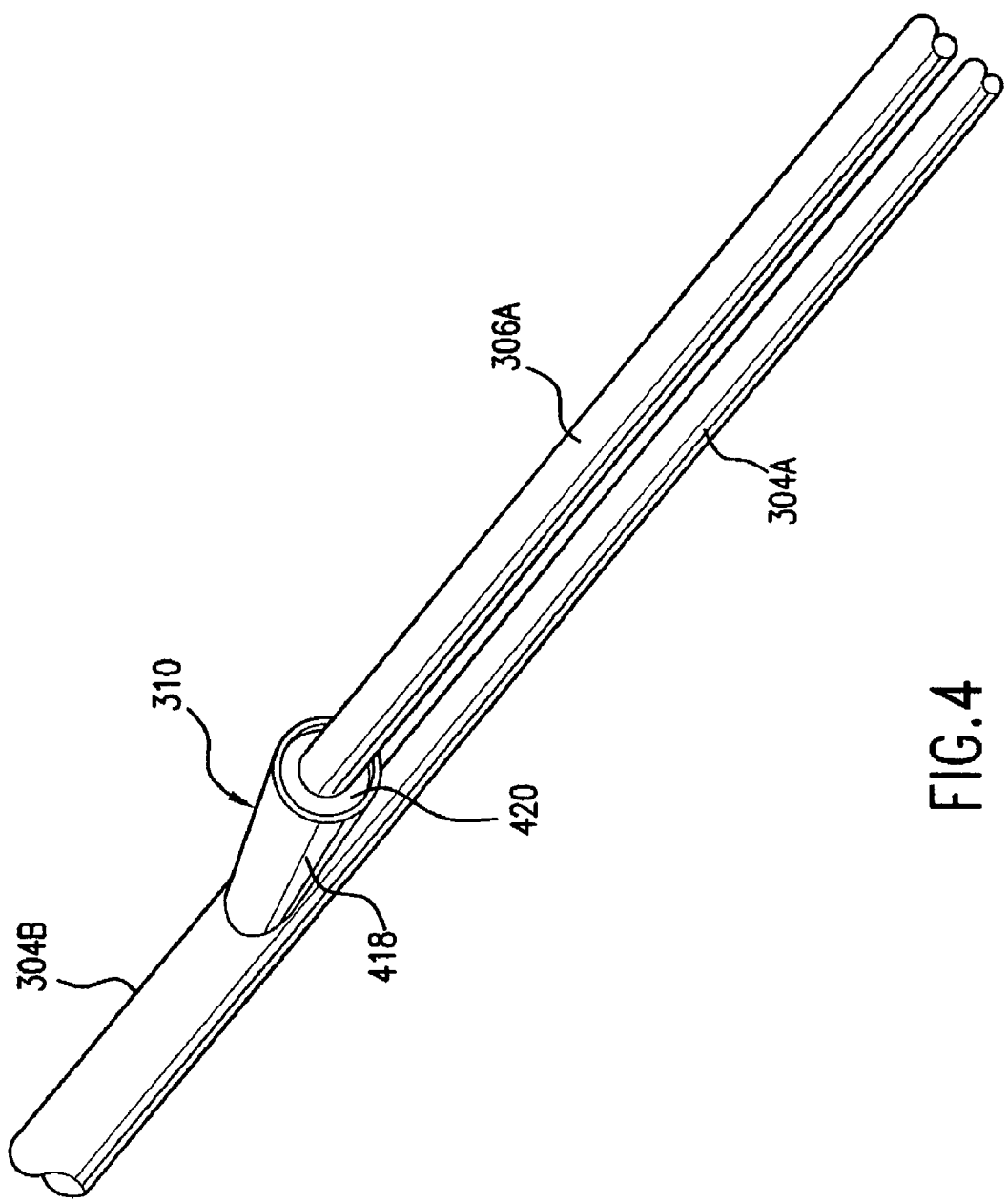
FIG. 4 is an enlarged view of a proximal portion of the catheter shown in FIG. 3.

FIG. 4 is an enlarged view of conversion joint 310 depicted in FIG. 3. Conversion joint 310 comprises a female fitting 418, which receives a male fitting 420 disposed upon distalmost end of guidewire shaft detachable portion 306A. Male fitting 420 of guidewire shaft 306 provides a snap-fit with female fitting 418 to allow the two shaft portions to snap-release or snap-lock.

Therefore, if a catheter exchange is required, proximal guidewire shaft 306A is unsnapped from conversion joint 310 such that guidewire 108 may be held in place while catheter 300 is pulled out thereover. If, on the other hand, a guidewire exchange is required, guidewire shaft detachable portion 306A is slid onto guidewire 108, and male fitting 420 of proximal guidewire shaft 306A is snap-locked into female fitting 418 of conversion joint 310.

Figure 5:
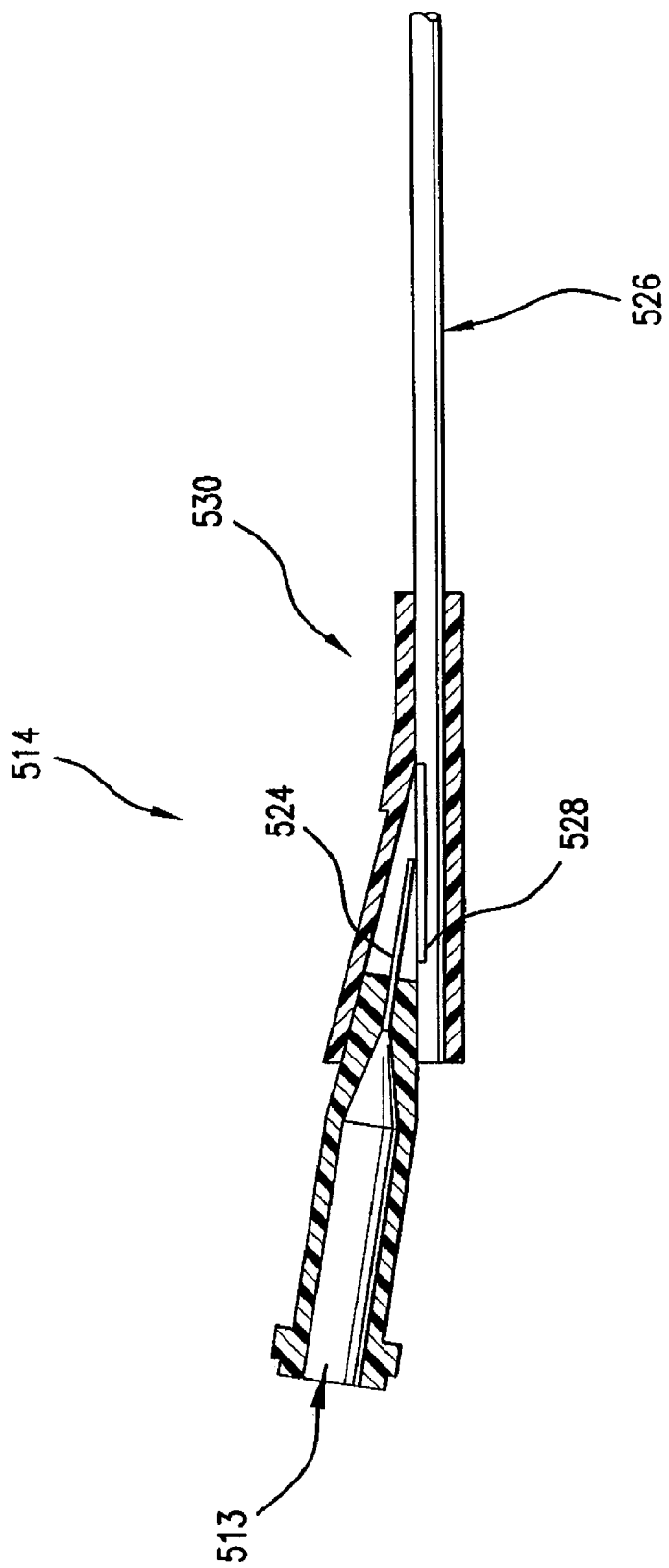
FIG. 5 is a perspective view of a MX guide member.

FIG. 5 depicts another embodiment of a MX guide member 514, which is also constructed to slide along guide member track 116 of guidewire shaft proximal portion 106A as shown in FIG. 1. Guide member 514 includes a proximal guidewire exit 513 for the guidewire to enter and exit the guidewire lumen. In this embodiment, guide member 514 comprises an internal hypotube 524, an external hypotube 526, a guide mandrel 528, and a cover 530. External hypotube 526 is disposed about proximal guidewire shaft detached portion 106A.

Internal hypotube 524 opens guide member track 116 as guide member 514 slides along proximal guidewire shaft detached portion 106A. Guidewire port 513 provides access to guidewire 108 into and out of the guidewire lumen. Internal hypotube 524 is attached to guide mandrel 528 and external hypotube 526. Guide mandrel 528 and external hypotube 526 ensure proper alignment of guide member 514 as it slides along the proximal guidewire shaft. Cover 530 provides structural stability and protects guide member 514 from damage.

To construct guide member 514, guidewire exit 513 and cover 530 are molded from acrylonitrile-butadiene-styrene (ABS) material. Internal hypotube 524, external hypotube 526 and guide mandrel 528 are made from 304 stainless steel hypotube. Guide mandrel 528 is soldered to an end of internal hypotube 524. This assembly is then soldered in such a manner as to provide access to a lumen within external hypotube 526. ABS guidewire exit 513 is adhesively bonded, using a cyanoacrylate, for example, to the internal hypotube, guide mandrel, and external hypotube assembly. Cover 530 is then adhesively bonded over, using for example cyanoacrylate, the above assembly. Guide member 514 is mounted externally of guidewire shaft proximal portion 106A by sliding the external hypotube 526 over guidewire shaft 106A.

Both embodiments of the present invention are primarily used in a manner similar to an OTW catheter. A balloon catheter made according to the MX embodiment of the present invention will first be described. First, a guidewire is tracked to a treatment site. Once in place, a distalmost tip of the balloon catheter of the present invention is threaded onto the indwelling guidewire. The MX guide member that acts as a moveable proximal guidewire exit and that is slidably positionable along the guide member track is placed, for description purposes, at its distalmost position, just proximal the conversion portion of the catheter. As the guidewire approaches the MX guide member, the catheter will be positioned so that the proximal end of the guidewire will go through the proximal guidewire exit of the guide member allowing for control of the guidewire distal of a proximal end of the catheter.

Holding and/or securing the guide member and the guidewire, the catheter is advanced into the vasculature. While the catheter is being advanced, the guidewire is enveloped within the guidewire lumen. Additionally, the guide member can be slidably advance proximally along the detached, proximal portion of the guidewire shaft as the catheter is advanced into the vasculature.

If at any point during the procedure, the catheter needs to be exchanged, this can be achieved by simply pulling the catheter device out of the vasculature while holding and sliding the guide member distally along the guide member track toward the conversion portion of the catheter. As the catheter is pulled out, guidewire control will switch from proximal to of the conversion section to a distalmost tip of the catheter. Therefore, the catheter can be removed entirely from the guidewire without losing guidewire control or position allowing another device to be slid onto the indwelling guidewire.

If on the other hand, the guidewire needs to be exchanged, it simply requires pulling the indwelling guidewire proximally out of a proximalmost positioned guide member while holding the catheter in position. The new guidewire may be forward loaded into the guidewire exit, tracked through the catheter, and positioned at the treatment site.

Alternatively, use of a snap-fit embodiment of the present invention will now be described. The use of a balloon catheter made according to the snap-fit embodiment is similar to that of the MX embodiment described above. The guidewire is positioned within the patient's vasculature and the distalmost tip of a catheter according to the present invention is backloaded over the proximal end of the guidewire. The catheter is advanced and manipulated so that the proximal end of the guidewire will exit through the female fitting of the conversion joint, i.e., the snap-fit juncture. The detached, proximal portion of the guidewire shaft is of course separated from the catheter at the conversion joint during this portion of the procedure. Thus, the proximal end of the guidewire is outside the catheter and allows an operator to maintain control over it. The detached portion of the guidewire shaft may be "snapped" into the conversion joint as necessary.

The catheter is then advanced into position for treatment of the patient. If the catheter requires changing, the guidewire is held in position and the catheter is pulled out over the guidewire, removed from the guidewire, and another device is used in a similar manner. To exchange the guidewire, the detached, proximal portion of the guidewire shaft, having been removed, is slid onto the guidewire and the distalmost tip of the proximal portion of the guidewire shaft having the male fitting is snap-locked into the female fitting of the conversion joint. This allows the original guidewire to be removed and a replacement guidewire to be front loaded into the proximal end of the guidewire lumen and into position.

Thus, an advantage of the presently-described design is that unlike RX catheters, the design of the proximal guidewire shaft prevents tangling of the guidewire with the inflation shaft. In addition, the presently-described design allows for simple and fast catheter and guidewire exchange.

While this invention has been particularly shown and described with reference to preferred embodiments thereof, it will be understood by those skilled in the art that various changes in form and details may be made therein without departing from the spirit and scope of the invention.

What is claimed is:

1. A catheter comprising:
a full-length inflation shaft having a proximal portion, a distal portion, and an inflation lumen;
a full-length guidewire shaft having a proximal portion, a distal portion, and a guidewire lumen, wherein the proximal portion of the guidewire shaft and the proximal portion of the inflation shaft are detached; and
a conversion bond that secures the guidewire shaft to the inflation shaft located at a distal end of the detached proximal portions of the guidewire and inflation shafts, wherein distal of the conversion bond the distal portion of the guidewire shaft is positioned within the inflation lumen of the distal portion of the inflation shaft.

2. The catheter of claim 1, further including a continuous longitudinal slot in the proximal portion of the guidewire shaft that extends from a proximal end to a distal end thereof.

3. The catheter of claim 2, further including a guide member, wherein the guide member further includes a proximal guidewire exit, wherein the guide member slides along the slot in the proximal portion of the guidewire shaft.

4. The catheter of claim 1, wherein the guidewire shaft is made from one continuous tube of a polymeric material.

5. The catheter of claim 4, wherein the polymeric material is HDPE.

6. The catheter of claim 1, wherein the guidewire shaft comprises at least two tubes, wherein one tube is the proximal portion and another tube is the distal portion of the guidewire shaft.

7. A catheter comprising:
a flexible first tube having a proximal end and a distal end;
a flexible second tube having a proximal portion and a distal portion, wherein the proximal portion of the second tube is detached from the first tube;
a flexible third tube being coaxial with said distal end of said first tube; and
a conversion bond, wherein the distal end of the first tube is bonded to a distal end of the detached proximal portion of the second tube and a proximal end of the third tube, such that the distal portion of the second tube is coaxially arranged within the third tube distal of the conversion bond.

8. The catheter of claim 7, further including a continuous longitudinal opening, wherein the longitudinal opening runs from a proximalmost portion to a distalmost portion of the detached, proximal portion of the second tube.

9. The catheter of claim 8, further including a guide member, wherein the guide member includes a guidewire exit, wherein the guide member slides along the opening in the detached, proximal portion of the second tube to allow access to a guidewire along the length thereof.

10. A catheter comprising:
an inflation shaft having a proximal portion, a distal portion, and an inflation lumen; and
a fUll-length guidewire lumen having a detachable proximal shaft portion and a distal shaft portion, wherein the proximal guidewire shaft portion includes a male fitting that is snap-fit with a female fitting of a conversion joint component of the catheter, wherein the proximal guidewire shaft portion and the conversion joint component are snap-releasable from one and other and snap-lockable together.

11. The catheter of claim 10, wherein the proximal portion of the inflation shaft is comprised of a hypotube and the distal portion of the inflation shaft is comprised of a polymer.

* * * * *